United States Patent [19]
Redmond et al.

[11] Patent Number: 4,904,236
[45] Date of Patent: * Feb. 27, 1990

[54] FLUID FLOW CONTROL VALVE

[75] Inventors: Russell J. Redmond, Goleta; Claude Vidal, Santa Barbara, both of Calif.

[73] Assignee: VIR Engineering, Goleta, Calif.

[*] Notice: The portion of the term of this patent subsequent to Nov. 1, 2005 has been disclaimed.

[21] Appl. No.: 189,761

[22] Filed: May 3, 1988

Related U.S. Application Data

[63] Continuation-in-part of Ser. No. 9,516, Jan. 30, 1987, Pat. No. 4,781,674.

[51] Int. Cl.⁴ .................................. A61M 5/00
[52] U.S. Cl. ............................. 604/9; 604/247; 137/854
[58] Field of Search ........................ 604/8–10, 604/169, 247, 185; 137/854; 251/297

[56] References Cited

U.S. PATENT DOCUMENTS

| | | | |
|---|---|---|---|
| 2,646,059 | 7/1953 | Wittner et al. | 137/854 |
| 3,037,522 | 6/1962 | Millan | 137/854 |
| 3,085,591 | 4/1963 | Schneider | 137/854 |
| 3,403,696 | 10/1968 | Pynchon | 137/854 |
| 3,648,728 | 3/1972 | Perry et al. | 137/854 |
| 3,768,508 | 10/1973 | Schulte | 604/9 |
| 4,550,749 | 11/1985 | Krikorian | 137/854 |
| 4,560,375 | 12/1985 | Schulte et al. | 604/9 |
| 4,609,006 | 9/1986 | Parkison et al. | 137/854 |
| 4,636,194 | 1/1987 | Schulte et al. | 604/8 |
| 4,675,003 | 6/1987 | Hooven | 604/9 |

Primary Examiner—Dalton L. Truluck
Assistant Examiner—Denise W. DeFranco
Attorney, Agent, or Firm—James E. Brunton

[57] ABSTRACT

A fluid flow control device for controling the flow of fluid from one region of the body to be drained to another region. The device includes a rigid cartridge combined with an elastomeric valve element. The design of the cartridge and valve element are such that the cartridge incorporates a seat and when the valve element is properly positioned within the valve body by a novel positioning arrangement it has sufficient spring force to push against the seat, thus creating a seal. The valve element ensures uni-directional flow as well as creating a set resistance to that flow. The unit can be easily assembled without the use of adhesives and in one configuration, the valve can be "tuned" to a desired pressure as a final assembly step. Combining two of the basic valving assemblies in series with an elastomeric section therebetween results in a valve system which can actively pump fluid downstream by squeezing the central connecting section.

18 Claims, 4 Drawing Sheets

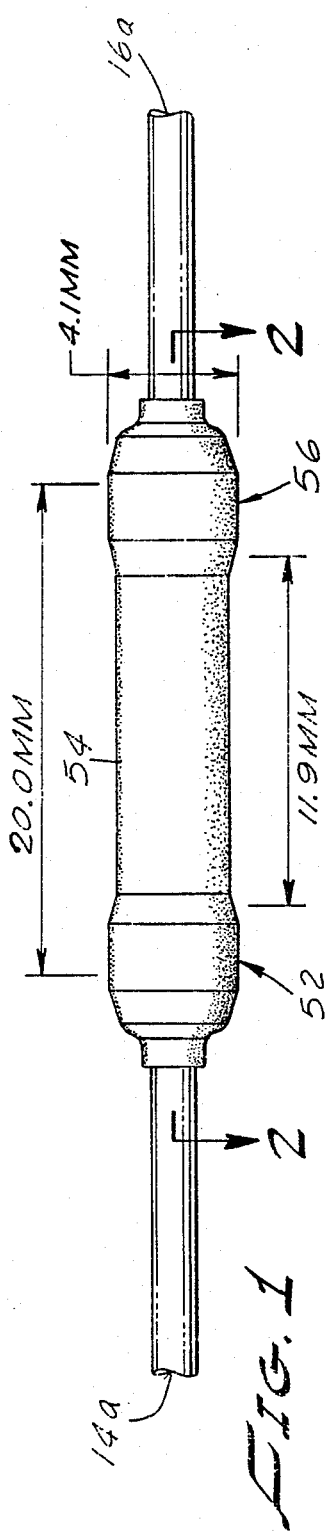
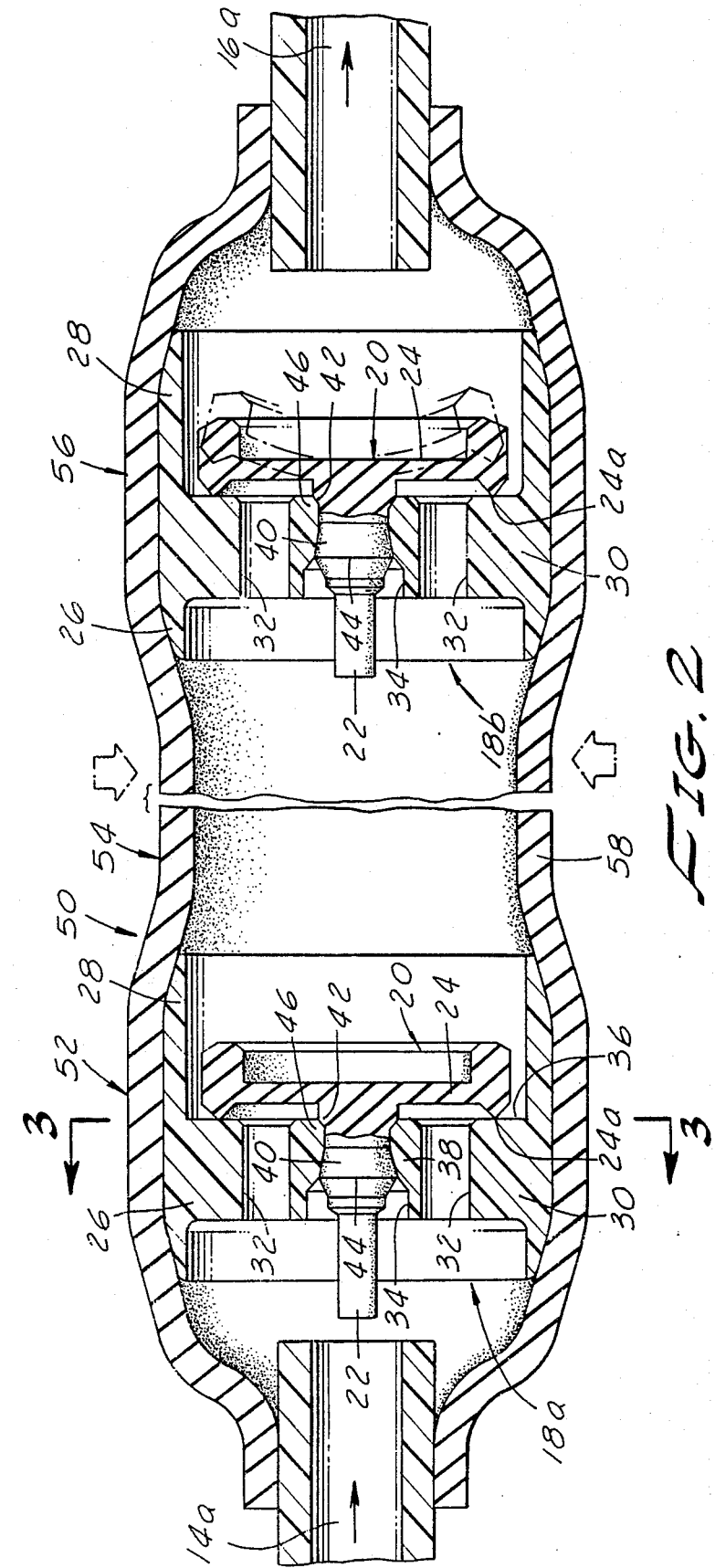

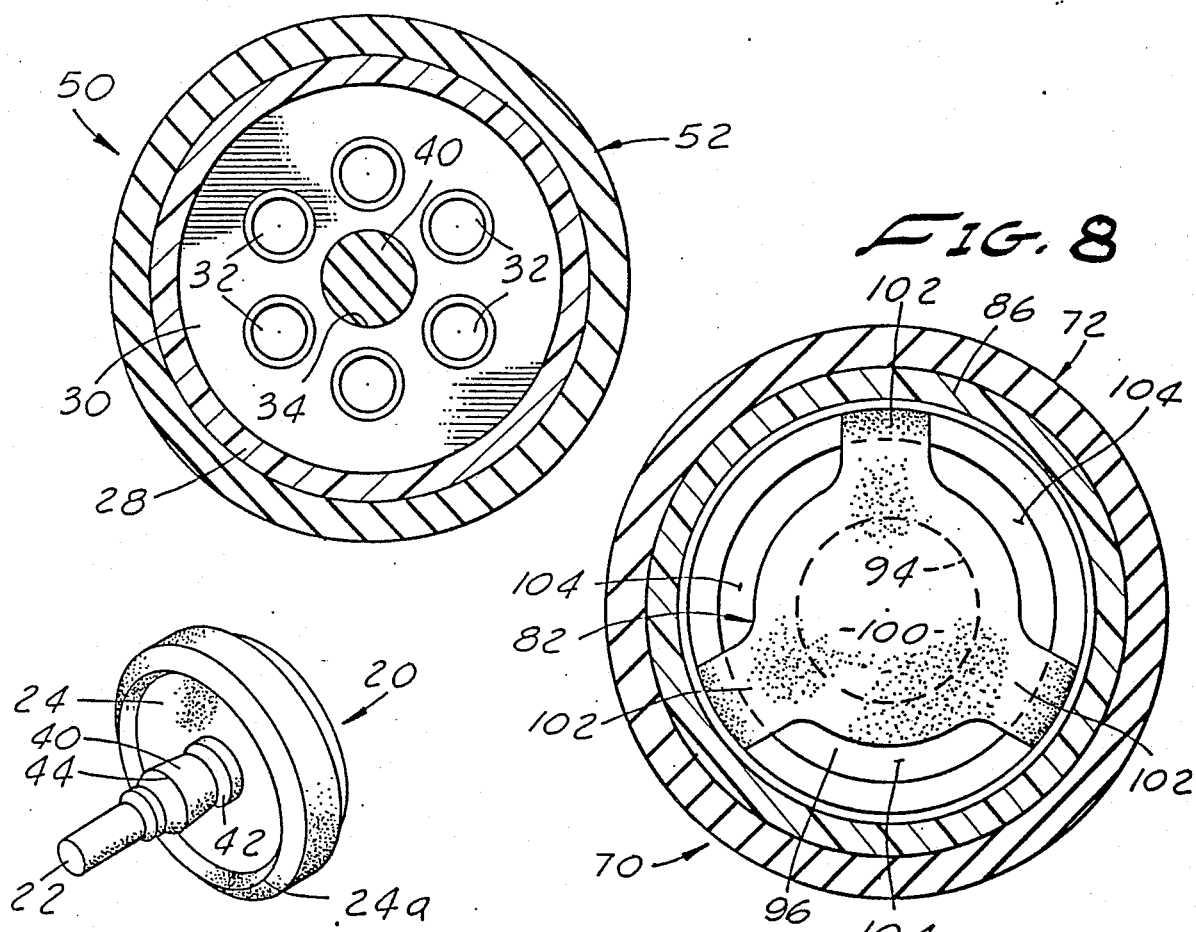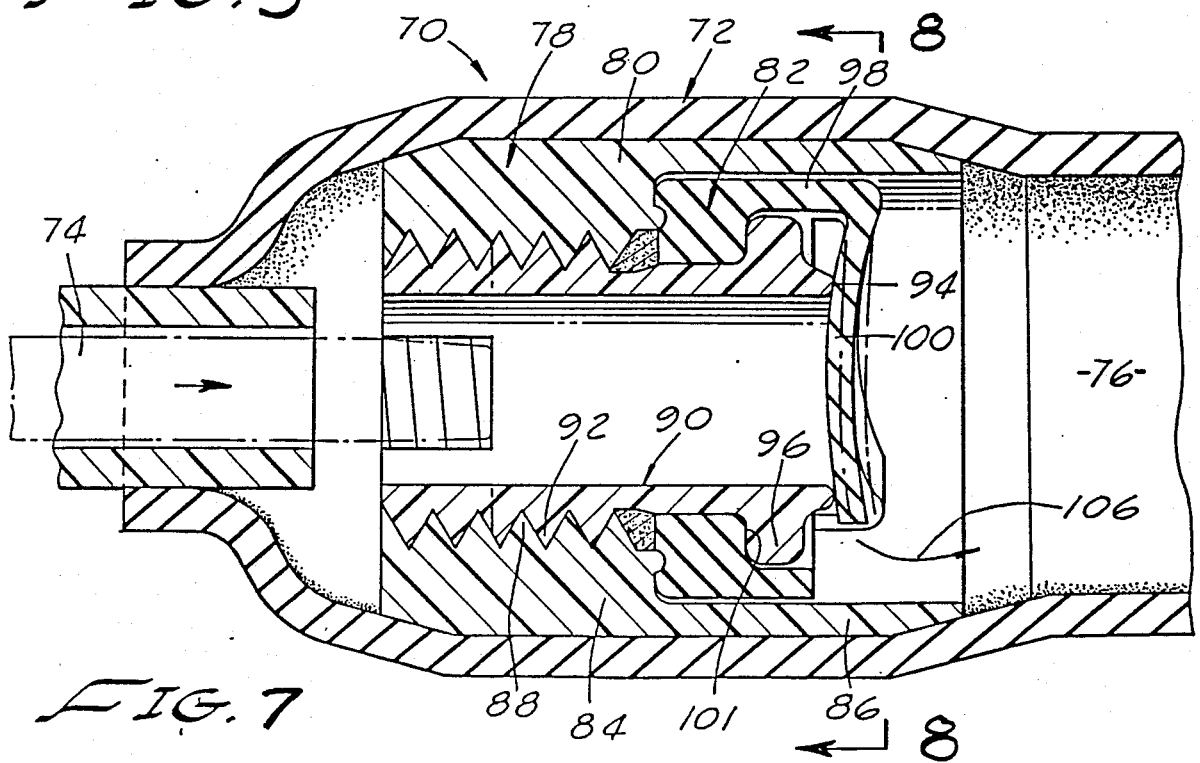

FLUID FLOW CONTROL VALVE

BACKGROUND OF THE INVENTION

This is a continuation-in-part of copending application Ser. No. 07/009,516 filed Jan. 30, 1987 now U.S. Pat. No. 4,781,674.

1. Field of the Invention

The present invention relates generally to valves for controlling fluid flow. More particularly, the invention concerns valves for use in the controllable release of entrapped body fluids.

2. Discussion of the Prior Art

In certain instances the human body fails to properly drain fluids from its cavities. For example, in an ailment known as hydrocephalus, cerebrospinal fluid is not properly drained from the brain. As a consequence, the patient may suffer an abnormal expansion of the cerebral ventricles, an enlargement of the skull and, if the condition is not corrected, atrophy of the brain. One of the most successful devices developed in the past for draining fluids from body cavities is described in U.S. Pat. No. 4,364,395 issued to one of the present co-inventors. U.S. Pat. No. 3,111,125 issued to Schulte and U.S. Pat. No. 3,595,240 issued to Mishler describe other prior art drainage apparatus. The devices disclosed in the Schulte patent comprise a combined pump and check valve. The device is disposed between a drainage catheter which is inserted into the cranium and a shunt tube with a check valve which generally discharges into the heart.

Drawbacks of many of the prior art drainage devices include clogging, valve degradation and failure as a function of time. Additionally, many of the prior art devices are bulky, difficult to surgically emplace and fail to properly control the amount of fluid drained from the body cavity. In this latter regard, it has been postulated that ideally the drainage device should precisely sense the fluid pressure generated in the body cavity to be drained and permit drainage to occur only when the fluid pressure in the body cavity reaches a predetermined level.

The apparatus of the present invention overcomes the drawbacks of the prior art devices by providing a device which is compact, highly reliable in operation and one which remains closed until a predetermined pressure in the body cavity to be drained is reached. Further, in one embodiment of the fluid flow control valve of the present invention, the valve assembly can be "tuned" to a desired opening pressure as a final assembly step. Additionally, as will be better understood from the discussion which follows, combining two of the valve assemblies of the basic fluid flow control device of the invention in series with an elastomeric section therebetween permits the apparatus to be used to actively pump fluid downstream by squeezing the central connecting section.

SUMMARY OF THE INVENTION

It is an object of the present invention to provide a fluid flow control device for controlling the flow of fluid from one region of the body to be drained to another region in which fluid will be permitted to flow through the device only upon a predetermined build-up of fluid pressure within the cavity to be drained.

It is another object of the invention to provide a device of the aforementioned character which ensures unidirectional fluid flow while at the same time creating a set resistance to that flow.

Another object of the invention is to provide a device as described in the preceding paragraphs in which the resistance to fluid flow through the device is precisely controlled by the unique design of the valve body of the device which carries the valve element.

Another object of the invention is to provide a device of the character described in which the valve body includes a rim portion configured to protect the valve element from needle puncture and manipulation damage.

Still another object of the invention is to provide a fluid flow control device which is very small, highly reliable in use, embodies a minimum number of component parts and one which can be completely assembled without the use of adhesives.

Another object is to provide an alternate form of the apparatus of the invention in which two valve assemblies in the basic configuration can be combined in series to provide a valve system which can actively pump fluid downstream.

Yet another object of the invention is to provide another alternate form of fluid flow control device which is adjustable so that the resistance to fluid flow offered by the valving element of the device can be easily and precisely adjusted during the final assembly step.

In summary, the fluid flow control device of the present invention comprises a rigid cartridge, or valve body, combined with an elastomeric valve element. The design of the cartridge and valve element are such that the cartridge incorporates a seat and the valve element has sufficient spring force to push against the seat, thus creating a seal. This elastomeric spring ensures unidirectional flow as well as creating a set resistance to that flow. The unique valve/cartridge design allows the unit to be easily assembled without the use of adhesives and in one configuration, allows the valve to be "tuned" to a desired pressure as a final assembly step. Combining two of the basic valve/cartridge assemblies in series with an elastomeric section therebetween results in a valve system which can actively pump fluid downstream by squeezing the central connecting section. In one form of the invention the seat is constructed from an elastomeric material. In another form, the seat is rigid and the valve element is constructed from an elastomeric material.

BRIEF DESCRIPTION OF THE DRAWINGS

FIG. 1 is a side elevational view of one form of the fluid flow control device of the present invention which can be used to controllably pump fluid downstream.

FIG. 2 is a greatly enlarged side elevational, cross-sectional view of the device of FIG. 1 taken along lines 2—2 of FIG. 1.

FIG. 3 is a cross-sectional view taken along lines 3—3 of FIG. 2 showing the construction of the valve element of the device.

FIG. 5 is a generally perspective view of the valve element of the device illustrated in FIGS. 1, 2 and 4.

FIG. 7 is a cross-sectional view of an alternate embodiment of the fluid flow control device of the invention wherein the resistance to fluid flow offered by the valve element can be adjusted.

FIG. 8 is a cross-sectional view taken along lines 8—8 of FIG. 7 showing the configuration of the valve element of this latter form of the invention.

DESCRIPTION OF THE INVENTION

Figure 4:
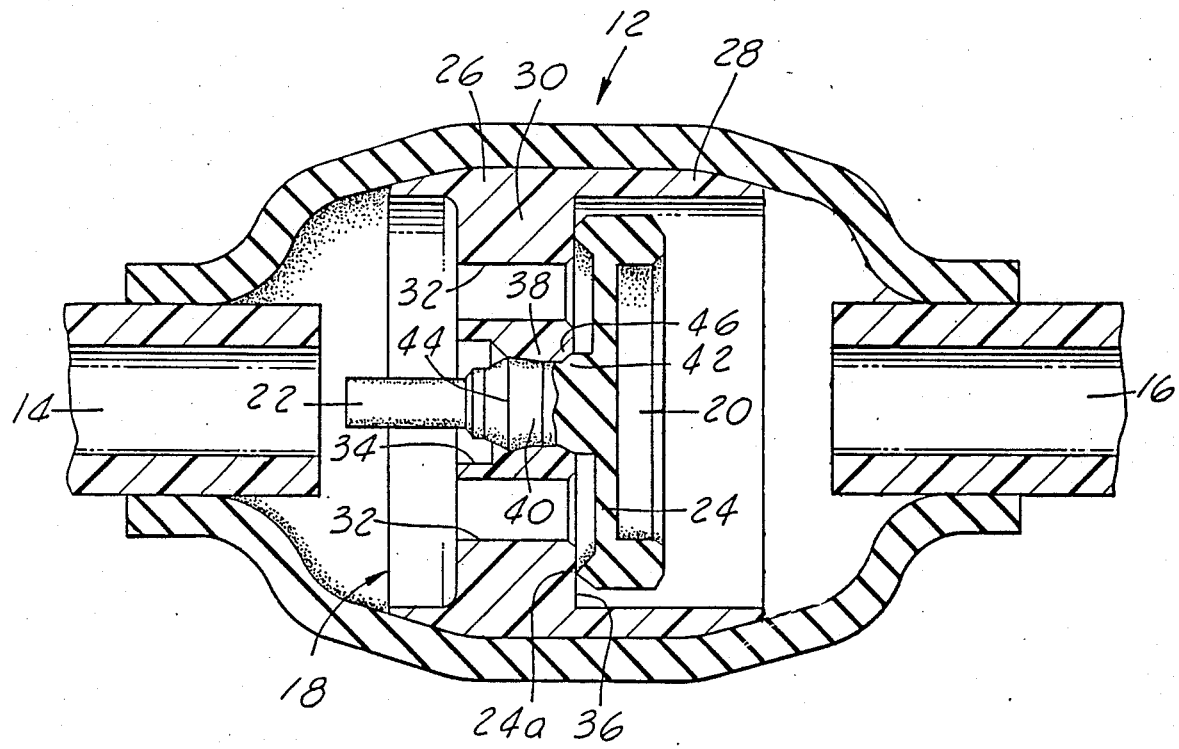
FIG. 4 is a cross-sectional view of a different form of fluid flow control device of the invention embodying one rather than two valving assemblies.

Referring to the drawings and particularly to FIGS. 1, 2 and 4, these figures depict two basic forms of the apparatus of the invention. The apparatus shown in FIG. 4 embodies a single valving assembly to control fluid flow through the apparatus. The form of the apparatus shown in FIGS. 1 and 2 embodies two valving assemblies arranged in series and disposed within an elongated housing, the intermediate portion of which is constructed of a yieldably resilient material. With this construction, squeezing the center portion of the apparatus permits fluid to be actively pumped downstream of the apparatus in the direction of the arrows.

Referring first to the embodiment of the invention shown in FIG. 4, this basic form of the device of the invention comprises a housing 12 having a fluid inlet 14 and a fluid outlet 16. Carried within housing 12 intermediate the fluid inlet and the fluid outlet is a valve assembly generally designated by the numeral 18. Valve assembly 18 comprises a valve member, or element, 20 having an elongated longitudinally extending stem 22 and an integrally formed, elastomeric valve element 24. The valve assembly further includes a valve body 26 comprising a rim portion 28 which is closely receivable within housing 12 and a transversely extending web portion 30. As best seen by referring to FIG. 3, web portion 30 is provided with a plurality of circumferentially spaced fluid passageways 32 extending through the web portion. Web portion 30 is also provided with a central bore 34 which extends through the web portion 30. The configuration of this central bore comprises an important aspect of the invention which will be discussed in greater detail hereinafter.

The face of the web portion 30, which is disposed on the outlet side of the device, comprises a valve seat 36 which is engageable by the annular rim portion 24a of the valve element 24 to block fluid flow from the inlet 14 through passageways 32 toward the outlet 16. Valve element 24 is preferably constructed of an elastomeric material and is movable from the closed position shown in FIG. 4 to an open position wherein the rim portion 24a of the valve element 24 is moved out of engagement with the valve seat 36 so as to permit flow of fluid through passageways 32 toward outlet 16.

Forming an important aspect of the present invention is valve member positioning means for precisely positioning the valve element 20 within the valve body 26. In the form of the invention shown in FIG. 4, this positioning means comprises a specially configured, reduced diameter portion 38 formed within the central bore 34 which extends through web portion 30. Reduced diameter portion 38 defines a cylindrical section of predetermined length which section is adapted to closely receive a uniquely configured, enlarged diameter portion 40 formed on the valve stem 22 intermediate its extremities.

As best seen by also referring to FIG. 5, the valve stem 22 includes a first circumferentially extending shoulder 42 formed proximate valve element 20 and a second, larger diameter shoulder 44 formed near the center of the stem. As indicated in FIG. 4, shoulder 42 is adapted to engage stop means formed on the cylindrical section 38 of the web portion, which stop means comprises a further part of the positioning means of the invention. As can be seen by referring to FIG. 4, in the embodiment of the invention thereshown, the stop means is provided in the form of an annular shaped shoulder 46 formed proximate the outlet side extremity of cylindrical section 38.

In assembling the apparatus shown in FIG. 4, the valve stem 22 is inserted through the central bore 34 formed in the web portion of the valve body. Upon then exerting a pulling force on stem 22 in the direction of fluid inlet 14, the valve member can be moved into the proper position within the valve body. By predetermining the length of the reduced diameter cylindrical portion 38 of the web and the length of the intermediate portion of the valve stem that is the portion between diameter 44 and stop 42, the valve member can be precisely positioned within the unit so that the desired resistive force, or spring action, is built into the valve element tending to bias it against movement away from the valve seat 36.

As indicated in FIG. 4, when the valve member is correctly positioned within the web portion of the valve body, the shoulder 42 is in engagement with shoulder 46 provided on the web portion and the enlarged diameter shoulder 44 has just cleared the edge of the cylindrical portion 38 of the transverse web. The yieldably resilient nature of the material from which the valve member is formed will cause the shoulder 44 to spring radially outwardly within central bore 34 and thereby securely hold the valve member in precisely the correct position within the valve body. Shoulder 42 prevents undue stretching of the valve stem, but permits sufficient stretching for shoulder 44 to clear the edge of cylindrical section 38. It is apparent that by varying the length of the cylindrical section 38, greater or lesser resistive force can be built into the valve element thereby enabling regulation of the amount of fluid pressure required to move the valve element into its second position where it is spaced apart from the valve seat.

Turning now to FIGS. 1 and 2, a second embodiment of the apparatus of the present invention is thereshown. In this form of the invention, two identical valve assemblies are arranged in series within an elongated housing generally designated by the numeral 50. The two valve assemblies are of identical construction to the valve assemblies described in the preceding paragraphs and like numerals are used in FIGS. 2 and 3 to identify like component parts.

Housing 50 comprises first, second and third portions 52, 54 and 56 respectively. A fluid inlet 14a is in communication with first portion 52 and a fluid outlet 16a is in communication with third portion 56. The first valve assembly, generally designated by the numeral 18a, is carried within first portion 52 of housing 50 intermediate the fluid inlet 14a and the second portion 54 of the housing 50. A second valve assembly, generally designated by the numeral 18b, is carried within third portion 56 of housing 50 intermediate fluid outlet 16a and second portion 54 of the housing 50. Third portion 54 of the housing comprises a yieldably deformable outer wall 58 which is movable from a first generally cylindrical configuration to a second diametrically compressed configuration. By squeezing intermediate section 58, fluid can be drawn into the central portion 58 through inlet 14a and then expelled outwardly through fluid outlet 16a. In this way, fluid can conveniently be pumped downstream of the apparatus.

As previously mentioned, valve assemblies 18a and 18b are of identical construction to the valve assembly illustrated in FIG. 4 and each includes valve members of the character shown in FIG. 5. Reference to FIG. 3 shows the one form of the arrangement of the fluid passageways 32 through the transverse web. However, it is to be understood that passageways of different configuration may be selected if desired. Assembly of the valve assemblies of FIGS. 1 and 2 is accomplished in a similar manner to the assembly of the valve member to the valve body as described previously in connection with the embodiment of the invention shown in FIG. 4. Once again, precise control over the length of the cylindrical section 38 of each of the valve assemblies and the precise positioning of the stop means on the cylindrical section enables the valve member to be positioned within the valve body in a predetermined manner so that the desired resistive force is exerted by the valve element against fluid under pressure entering the apparatus through inlet passageway 14a. By varying the length of the cylindrical section 38 of each of the valve assemblies 18a and 18b, the amount of pressure necessary to open the valve assemblies can be precisely regulated.

Referring to FIG. 1, the overall configuration of the apparatus of this second form of the invention is thereshown. As indicated by the dimensions in FIG. 1, which are exemplary only, the apparatus of the invention is quite compact thereby minimizing the difficulties of surgical emplacement. It is to be understood that the size of the apparatus can be varied depending on the particular end use of the apparatus.

In the embodiments of the invention shown in FIGS. 1 through 5, the housing of the apparatus is preferably constructed from a durable, yieldably resilient moldable material. Similarly, the valve member of each form of the apparatus is preferably constructed of a yieldably resilient moldable material such as plastic or soft rubber. The valve body may be constructed of various materials including plastic and metal. In this regard, it is to be understood that the valve seat formed on the valve body may be constructed of a yieldably resilient material and the portion of the valve member which engages the valve seat may be constructed of a rigid material. Conversely, the valve seat may be constructed of a rigid material while the portion of the valve member which engages the valve seat can be constructed of a yieldably resilient material.

Figure 6:
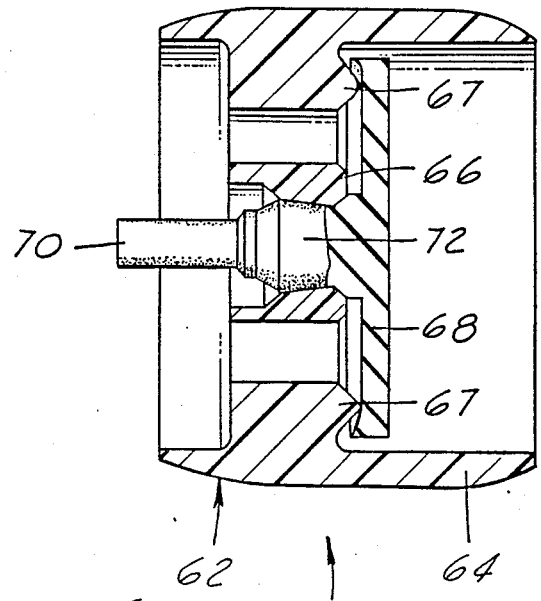
FIG. 6 is a fragmentary cross-sectional view of an alternate form of valving assembly of the present invention embodying a rigid rather than elastomeric seat.

Turning now to FIG. 6, a slightly different form of valve assembly of the present invention is thereshown and generally designated by the numeral 60. This form of valve assembly includes a valve body 62 having a rim portion 64 which is closely receivable within the outer housing of the apparatus and a transversely extending web portion 66. Web portion 66 is of similar construction to that shown in FIG. 4, but the valve seat arrangement is slightly different. In this particular embodiment of the invention, the valve seat, designated by the numeral 67, is constructed of a rigid material and comprises a rearwardly extending protuberance which is adapted to engage a yieldably resilient valve element 68. Valve element 68 is formed integrally with a longitudinally extending valve stem 70. Valve stem 70 includes a central portion 72 which is of an identical construction to that described in connection with FIG. 4.

Basically the embodiment of the valve assembly shown in FIG. 6 merely illustrates a construction wherein the valve seat is rigidly formed while the valve member 68 is formed of a relatively thin yieldably deformable elastomeric material. Once again, the positioning means of the valve assembly ensures that the valve member will be carried within the valve body so that a predetermined spring, or resistive force, is built into the valve element resisting its movement away from the valve in response to fluid under pressure entering the device through the fluid inlet.

Referring to FIGS. 7 and 8, yet another embodiment of the apparatus of the present invention is thereshown. This form of the apparatus, generally designated by the numeral 70, is adjustable and comprises a housing 72 having a fluid inlet 74 and a fluid outlet 76. Carried within housing 72 is a valve assembly 78 which comprises a valve body 80 and a valve member 82.

Valve body 80 includes a longitudinally extending, generally cylindrically shaped first, or outer member, 84 having a rim portion 86 and an internally threaded portion 88. The valve body also includes a longitudinally extending generally cylindrically shaped second, or inner, member 90 having an externally threaded portion 92 adapted to threadably mate with threaded portion 88 of first member 84. Second member 90 also has a rigid valve seat 94 formed proximate the extremity thereof nearest the outlet passageway 76 of the unit. Second, or inner member, 90 also includes a circumferentially extending shoulder 96, the purpose of which will presently be described.

The valve member 82 of the present embodiment of the invention is carried intermediate first and second body members 80 and 90 and includes a generally cylindrically shaped body portion 98 and a yieldably resilient valve member or element 100. A shoulder 101 is formed on body portion 98 for engagement with shoulder 66 of inner member 90. Valve element 100 is integrally formed with the body portion 98 and is normally disposed in sealing engagement with valve seat 94. However, the valve element is movable away from the valve seat into a second position indicated by the phantom lines in FIG. 7 in response to fluid pressure exerted thereon in the direction of the arrow of FIG. 7.

Turning to FIG. 8, it can be seen that the central portion of the valve element 100 is normally in pressural engagement with the valve seat 94. Formed at the outer periphery of the valve element are three equally spaced legs 102 which connect the valve element with the valve body 98. With this construction, circumferentially spaced fluid passageways 104 are formed to enable the flow of fluid through the unit in the direction of the arrow 106 (FIG. 7) when the valve element is moved into its second position spaced apart from the rigid valve seat 94.

An important aspect of the apparatus of the invention shown in FIGS. 7 and 8 is its ability to be precisely adjusted, or fine tuned, at time of assembly. More particularly, threadable movement of the inner portion of the valve body with respect to the outer portion results in pressure being exerted upon the valve member 82 whereby the degree of resistance, or springiness, offered by the valve element 100 against movement into its second position wherein it is spaced apart from the valve seat can be precisely adjusted to meet particular end product applications. This adjustability feature, for the first time, provides a unit which can be precisely tuned to the particular patient's needs so as to ensure that the valve will open to permit fluid drainage only when a predetermined fluid pressure exists within the body cavity to be drained.

Figure 9:
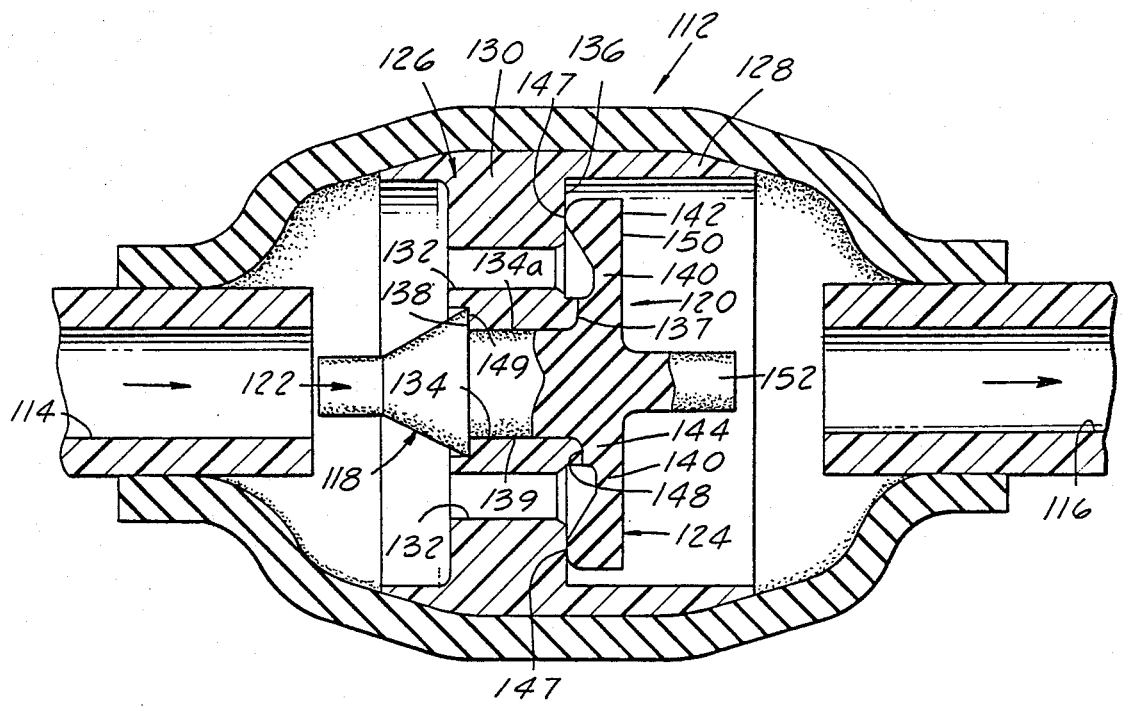
FIG. 9 is a cross-sectional view of another form of fluid flow control device of the invention embodying a differently configured valving element.
Figure 10:
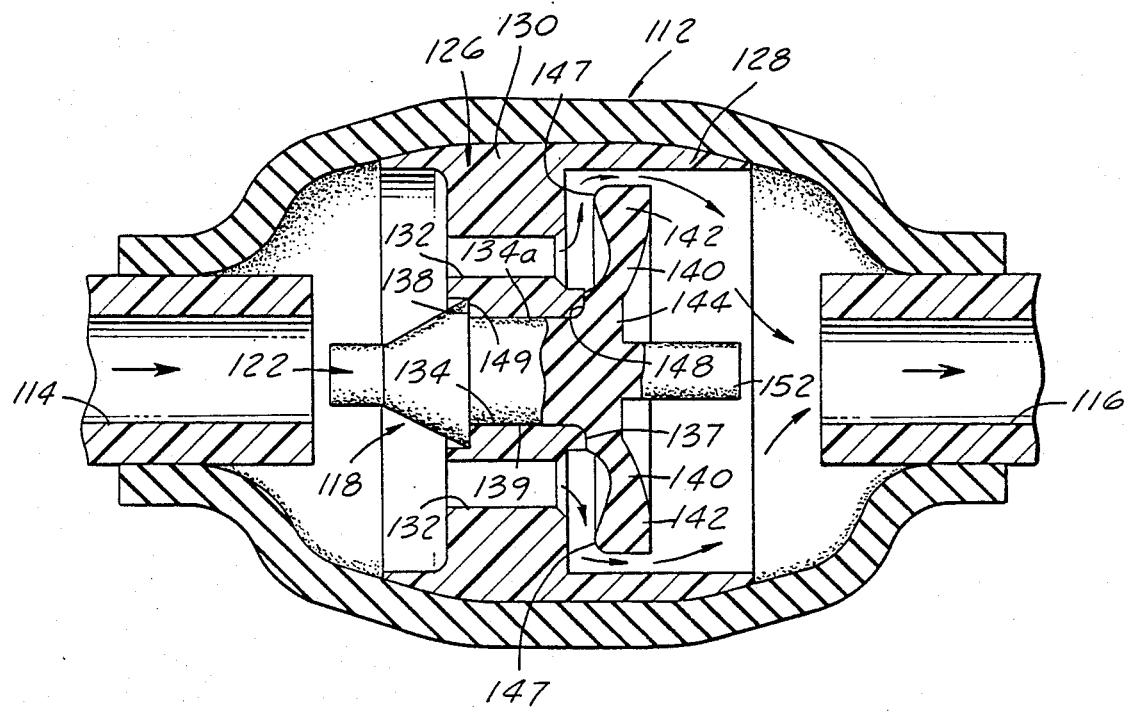
FIG. 10 is a cross-sectional view similar to FIG. 9 but showing the valving element in an open position.

Referring now to FIGS. 9 and 10 of the drawings, another form of the apparatus of the invention is there shown. The apparatus shown in these figures is similar in many respects to the apparatus shown in FIG. 4, but includes a valve element of different construction.

The device of the invention shown in FIG. 9 comprises a housing 112 having a fluid inlet 114 and a fluid outlet 116. Carried within housing 112 intermediate the fluid inlet and the fluid outlet is a valve assembly generally designated by the numeral 118. Valve assembly 118 comprises a valve member 120 having an elongated longitudinally extending stem 112 and an integrally formed, elastomeric valve element 124. The valve assembly further includes a valve body 126 comprising a rim portion 128 which is closely receivable within housing 112 and a transversely extending web portion 130. Web portion 130 is provided with a plurality of circumferentially spaced fluid passageways 132 extending through the web portion. Web portion 130 is also provided with a central bore 134 which extends through the web portion 130.

The face of the web portion 130, which is disposed on the outlet side of the device, comprises a generally planar valve seat 136 which is engageable by the valve seat engaging portion of the valve element 124 to block fluid flow from the inlet 114 through passageways 132 toward the outlet 116. Valve element 124 is preferably constructed of an elastomeric material and is movable from the closed position shown in FIG. 9 to the open position illustrated in FIG. 10, wherein the valve seat engaging portion of the valve element 124 is moved out of engagement with the valve seat 136 so as to permit flow of fluid through passageways 132 toward outlet 116. The specific configuration of the valve element 124, which will presently be described, comprises a very important feature of the device of this form of the invention.

Also forming an important aspect of the device is the valve member positioning means for precisely positioning the valve member 120 within the valve body 126. In the form of the invention shown in FIG. 9, this positioning means comprises an annular shoulder 137 provided on web portion 130 and a precisely located shoulder 138 formed within the central bore 134 which extends through web portion 130. Located between shoulders 137 and 138 is a cylindrical section 134a of predetermined length which section is adapted to closely receive a uniquely configured, enlarged diameter portion 139 formed on the valve stem 122 intermediate its extremities.

Considering now the unique configuration of the valve assembly of this embodiment of the invention, the valve element 124 thereof comprises a generally disc-shaped portion having a thin centrally disposed annular portion 140, a first annular portion 142 spaced radially outwardly from portion 140 and a second annular portion 144 spaced radially inwardly from portion 140. As indicated in FIG. 9, central portion 140 is generally of constant wall thickness and is disposed within a plane generally parallel to the plane of valve seat 136. First annular portion 142 is generally triangular shaped in cross-section and defines the previously mentioned valve seat engaging surface 147. Surface 147 provides a generally circular line of contact with the valve seat 136 and is maintained in constant pressural engagement with valve seat 136 in a manner presently to be described. As illustrated in FIG. 9, first annular portion 142 is considerably thicker than central portion 140. Second annular portion 144 is also thicker than central portion 140, but has a thickness somewhat less than that of first annular portion 142. Portion 144 defines a first shoulder 148, which, in a manner presently to be described, is maintained in engagement with shoulder, or stop, 137 provided on web portion 130. As previously mentioned valve stem 122 is integrally formed with valve element 124 and extends outwardly from portion 144, that is, toward inlet 114.

Valve stem 122 includes the previously mentioned enlarged diameter portion 139 which terminates in a second shoulder 149. Shoulder 149 is longitudinally spaced apart from first shoulder 148 by a precisely predetermined distance approximately equal to, and preferably slightly greater than, the length of cylindrical section 134a. With this construction the valve member will be held securely in position within the device with first shoulder 148 of the valve element in engagement with stop 137 on web portion 130 and with second shoulder 149 of the valve stem in engagement with shoulder 138 formed within central bore 134 of web portion 130.

It is very important to note that with the valve member held in position within the device in the manner shown in FIG. 9, the difference in the thickness of first annular portion 142 and second annular portion 144 of the valve element, coupled with the character of the elastomeric material, is such that the valve seat engaging surface 147 is continuously maintained in constant pressural engagement with the valve seat 136. At the same time the configuration of the valve element itself ensures that the planar rear surface 150 of the valve element, that is the surface nearer outlet 116, is normally disposed within a plane substantially parallel to the plane of the valve seat 136.

It is also to be noted that the thickness of central annular portion 140 is controlled such that when fluid flows through passageways 132 at a predetermined elevated pressure, central portion 140 will yieldably flex, or deform, in the manner shown in FIG. 10 to permit Fluid Flow past the valve element and toward outlet 116. It is apparent that by proper material selection, and by carefully controlling the relative thicknesses of the various annular portions of the valve element, the device can be designed to open and close only within precise fluid pressure ranges.

Another extremely important feature of this embodiment of the invention resides in the fact that when the valve opens the valve element yieldably deforms at the central annular portion 140 in a manner such that the valve seat engaging surface of annular portion 142 moves away from the valve seat in a direction substantially perpendicular to the plane of the valve seat. This important feature is not found in prior art devices which embody umbrella, or dome shaped valves such as the valves disclosed in U.S. Pat. No. 4,560,395 issued to Schulte et al. In devices such as the Schulte et al device, as the valve opens the peripheral portions of the valve follow an arcuate path relative to the seating surface rather than a path substantially perpendicular thereto as is the case with the device of the present invention. This fact is of great importance when the device of the invention is used for draining body fluids and of necessity must be very, very small. By not having to provide clearance for the opening of the valve along an arcuate path, the overall diameter of the valve housing can be reduced significantly. Accordingly, the inside diameter of rim portion 128 of the valve body can be constructed to have substantially the same outside diameter as that of valve element 124.

In assembling the apparatus shown in FIG. 4, the valve stem 122 is inserted through the central bore 134 formed in the web portion of the valve body. By then exerting a pulling force on stem 122 in the direction of fluid inlet 14, the valve member can be moved into the proper seating position within the valve body. By closely controlling the length of the reduced diameter cylindrical portion of the web and the length of the intermediate portion of the valve stem, that is the portion between shoulders 148 and 149, the valve member can be precisely positioned and positively secured within the unit. To assist in the assembly process and in molding of the valve assembly, a cylindrically shaped member 152 is integrally formed with the valve element and extends longitudinally from face 150.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A fluid flow control device for controlling the flow of fluid from one region of the body to be drained to another region, said device comprising a housing having a fluid inlet and a fluid outlet and a valve assembly carried within said housing intermediate said fluid inlet and said fluid outlet, said valve assembly comprising:
   (a) an elastomeric valve member including a valve stem and a valve element carried by said valve stem said valve element including a thin centrally disposed annular portion, a thicker first annular portion spaced radially outwardly from said central portion and defining a seat engaging surface, and a second annular portion spaced radially inwardly from said central portion, said second annular portion having a thickness less than the thickness of said first annular portion; and
   (b) a valve body, said valve body comprising a rim portion closely receivable within said housing and a transversely extending web portion, said web portion having a fluid passageway therethrough and including:
      (i) a valve seat for engagement by said valve element to control the flow of fluid through said fluid passageway; and
      (ii) valve member positioning means for positioning said valve member within said valve body so that said seat engaging surface of said first annular portion is normally maintained in pressural engagement with said valve seat.

2. A fluid flow control device as defined in claim 1 in which said valve member positioning means comprises a longitudinally extending central bore through said web portion defining a cylindrical section of predetermined length adapted to closely receive said valve stem.

3. A fluid flow control device as defined in claim 2 in which said valve stem includes a circumferentially extending first shoulder and in which said valve member positioning means further comprises stop means formed on said cylindrical section for engagement by said first shoulder of said valve stem.

4. A fluid flow control device as defined in claim 3 in which said stop means comprises an annular shoulder formed on said cylindrical section.

5. A fluid flow control device for controlling the flow of fluid from one region of the body to be drained to another region, said device comprising a housing having a fluid inlet and a fluid outlet and a valve assembly carried within said housing intermediate said fluid inlet and said fluid outlet, said valve assembly comprising:
   (a) an elastomeric valve member comprising:
      (i) a valve element including a thin centrally disposed annular portion, a first annular portion spaced radially outwardly from said central portion and defining a seat engaging surface, and a second annular portion spaced radially inwardly from said central portion, said second annular portion having a thickness less than the thickness of said first annular portion; and
      (ii) an integrally formed stem extending outwardly from said valve element, said stem including an enlarged diameter portion defining proximate one extremity a first circumferentially extending, shoulder;
   (b) a valve body comprising a rim portion closely receivable within said housing and a transversely extending web portion, said web portion having a fluid passageway therethrough and including:
      (i) a valve seat for engagement by said valve element to control the flow of fluid through said fluid passageway; and
      (ii) a central bore defining a cylindrical section of predetermined length and diameter for closely receiving said enlarged diameter portion of said valve member to position said valve member within said valve body so that said seat engaging surface of said first annular portion is normally maintained in pressural engagement with said valve seat.

6. A fluid flow control device as defined in claim 5 in which said valve stem is provided with a second circumferentially extending shoulder longitudinally spaced from said first shoulder and of a diameter slightly greater than the diameter of said cylindrical section.

7. A fluid flow control device as defined in claim 5 in which said web portion includes a circumferentially extending shoulder engageable by said first shoulder of said stem when said valve member is properly positioned within said valve body.

8. A fluid flow control device as defined in claim 5 in which said valve seat is constructed of an elastomeric material.

9. A fluid flow control device as defined in claim 5 in which said valve seat is constructed of a rigid, substantially non-deformable material.

10. A fluid flow control device as defined in claim 5 in which said valve body includes a longitudinally extending outer wall for enclosing said valve element and said enlarged diameter portion of said stem when said valve member is properly positioned within said valve body.

11. A fluid flow control device for controlling the flow of fluid from one region of the body to be drained to another region, said device comprising a generally cylindrically shaped housing having a fluid inlet and a coaxially aligned fluid outlet and a valve assembly carried within said housing intermediate said fluid inlet and said fluid outlet, said valve assembly comprising:
(a) an elastomeric valve member comprising:
  (i) a generally disc shaped valve element having substantially planar faces disposed in substantially parallel planes; and
  (ii) an integrally formed, substantially cylindrically shaped elongated stem extending from said valve element, said stem being yieldably deformable along its length and including an enlarged diameter portion of predetermined length having longitudinally spaced first and second shoulders;
(b) a valve body comprising a rim portion closely receivable within said housing and a transversely extending web portion, said web portion having a fluid passageway therethrough and including:
  (i) a valve seat for engagement by said valve element to control the flow of fluid through said fluid passageway; and
  (ii) a central bore defining a cylindrical section of predetermined length and diameter for closely receiving said enlarged diameter portion of said valve member to position said valve member within said valve body, said cylindrical section including a circumferentially extending edge having a diameter less than that of said second shoulder of said enlarged diameter portion of said stem, said respective lengths of said cylindrical section of said bore and of said enlarged diameter portion of said stem being such that upon exerting a pulling force on said stem, said stem will be yieldably deformed along it length and said second shoulder will engage said second edge of said cylindrical section to maintain said stem in a deformed state, whereby said valve element will exert a predetermined closing pressure upon said valve seat.

12. A fluid flow control device as defined in claim 11 in which said valve body includes a longitudinally extending, generally cylindrically shaped, outer wall for enclosing said valve element and said enlarged diameter portion of said stem when said valve member is properly positioned within said valve body.

13. A fluid flow control device for controlling the flow of fluid from one region of the body to be drained to another region, said device comprising a housing having a fluid inlet and a fluid outlet and a valve assembly carried within said housing intermediate said fluid inlet and said fluid outlet, said valve assembly comprising:
(a) an elastomeric valve member comprising:
  (i) a generally disc shaped valve element having a thin centrally disposed annular portion, a thicker first annular portion spaced radially outwardly from said central portion and defining a seat engaging surface, said first annular portion having a thickness greater than the thickness of said centrally disposed annular portion and a second annular portion spaced radially inwardly from said central portion and defining a first shoulder said second annular portion having a thickness less than the thickness of said first annular portion;
  (ii) an integrally formed, elongated stem extending from said second annular portion of said valve element, said stem including a first portion of predetermined length terminating in a second shoulder longitudinally spaced from said first shoulder;
(b) a valve body comprising a rim portion closely receivable within said housing and a transversely extending web portion, said web portion having a fluid passageway therethrough and including:
  (i) a generally planar valve seat for engagement by said seat engaging surface of said first annular portion of said valve element to control the flow of fluid through said fluid passageway; and
  (ii) a central bore defining a cylindrical section of predetermined length and diameter for closely receiving said first portion of said stem to position said valve member within said valve body, said cylindrical section including a circumferentially extending edge, said respective lengths of said cylindrical section of said bore and of said enlarged diameter portion of said stem being such that said second shoulder of said stem is maintained in engagement with said circumferentially extending edge and said seat engaging surface of said first annular portion is maintained in pressural engagement with said valve seat.

14. A fluid flow control device as defined in claim 13 in which said valve body includes a longitudinally extending, generally cylindrically shaped, outer wall for closely receiving said valve element.

15. A fluid flow control device as defined in claim 13 in which said centrally disposed annular portion is so constructed and arranged that upon a fluid pressure being exerted on said valve element by fluid flowing through said fluid passageway, said centrally disposed annular portion will be yieldably deformed in a manner that said seat engaging surface of said first annular portion will move away from said valve seat in a direction generally perpendicular to the plane of said valve seat.

16. A fluid flow control device as defined in claim 15 in which said centrally disposed annular portion is of a substantially constant, predetermined wall thickness and is disposed within a plane generally parallel to the plane of said valve seat.

17. A fluid flow control device as defined in claim 16, further including an elongated member integrally formed with said valve element and extending longitudinally therefrom in a direction opposite to that of said stem.

18. A fluid flow control device as defined in claim 17 in which said valve element includes a front face from which said stem extends and a generally planar rear face from which said elongated member extends.

* * * * *